United States Patent
Kadri et al.

(10) Patent No.: US 11,127,496 B2
(45) Date of Patent: Sep. 21, 2021

(54) CLINIC DESIGN AND CORRESPONDING PATIENT ENGAGEMENT TOOL

(71) Applicant: Kadri Medical Ltd., Windsor (CA)

(72) Inventors: Albert Kadri, Windsor (CA); Mohammed J. Ibrahim, Windsor (CA)

(73) Assignee: Kadri Medical Ltd., Windsor (CA)

( * ) Notice: Subject to any disclaimer, the term of this patent is extended or adjusted under 35 U.S.C. 154(b) by 0 days.

(21) Appl. No.: 16/112,835

(22) Filed: Aug. 27, 2018

(65) Prior Publication Data

US 2019/0108907 A1    Apr. 11, 2019

Related U.S. Application Data

(60) Provisional application No. 62/569,737, filed on Oct. 9, 2017.

(51) Int. Cl.
*G16H 40/20* (2018.01)
*G06K 19/06* (2006.01)
(Continued)

(52) U.S. Cl.
CPC ........... *G16H 40/20* (2018.01); *G06K 7/1417* (2013.01); *G06K 19/06037* (2013.01);
(Continued)

(58) Field of Classification Search
CPC ........ G16H 40/20; G16H 70/40; G16H 70/20; G16H 80/00; G06Q 10/10; G06Q 50/16;
(Continued)

(56) References Cited

U.S. PATENT DOCUMENTS

| | | |
|---|---|---|
| 5,748,907 A * | 5/1998 Crane | G06Q 10/06 705/2 |
| 2003/0230031 A1* | 12/2003 Lam | E04H 5/02 52/79.1 |

(Continued)

OTHER PUBLICATIONS

McGough PM, Jaffy MB, Norris TE, Sheffield P, Shumway M. Redesigning your work space to support team-based care. Fam Pract Manag. Mar.-Apr. 2013;20(2):20-4. PMID: 23547610. (Year: 2013).*

(Continued)

*Primary Examiner* — Matthew Mikels
(74) *Attorney, Agent, or Firm* — The Dobrusin Law Firm, PC

(57) ABSTRACT

A clinic layout, corresponding computer program and companion mobile device application is provided. A physical layout for a clinic design is provided including a waiting room, reception area, modular pods, exam rooms, pharmacy, laboratory . . . etc. along with a corresponding flow arrow designed to optimize clinic efficiency and patient experience. A corresponding computer program and companion mobile device application is provided to work in combination with the physical layout of the client. The three components (physical design, computer program and companion mobile device application) work together to enhance coordination of care, increase patient involvement in care, while also increasing clinic efficiency by integrating the clinic layout and design such as described herein and above. The problem list, medication list, educational material, appointments, and the associated reminders provided to the patient will also be instrumental in improving health outcomes. This feature is incorporated into the computer program and companion mobile device application. A detailed explanation of each component can be found as described herein.

7 Claims, 7 Drawing Sheets

(51) Int. Cl.
*G06K 7/14* (2006.01)
*G06Q 10/10* (2012.01)
*G16H 70/40* (2018.01)
*G06Q 50/16* (2012.01)
*G06Q 50/22* (2018.01)
*G16H 70/20* (2018.01)
*G16H 80/00* (2018.01)

(52) U.S. Cl.
CPC ............. *G06Q 10/10* (2013.01); *G06Q 50/16* (2013.01); *G06Q 50/22* (2013.01); *G16H 70/20* (2018.01); *G16H 70/40* (2018.01); *G16H 80/00* (2018.01)

(58) Field of Classification Search
CPC . G06Q 50/22; G06K 19/06037; G06K 7/1417
USPC ................. 235/375–385, 435, 439, 454, 462
See application file for complete search history.

(56) References Cited

U.S. PATENT DOCUMENTS

2013/0054271 A1\* 2/2013 Langford ............... G06Q 50/24
705/3
2015/0019238 A1\* 1/2015 Felt ..................... G06F 19/3456
705/2

OTHER PUBLICATIONS

Gunn, et al. (2015). Designing Clinical Space for the Delivery of Integrated Behavioral Health and Primary Care. Journal of the American Board of Family Medicine : JABFM. 28 Suppl 1. S52-62. 10.3122/jabfm.2015.S1.150053. (Year: 2015).\*

\* cited by examiner

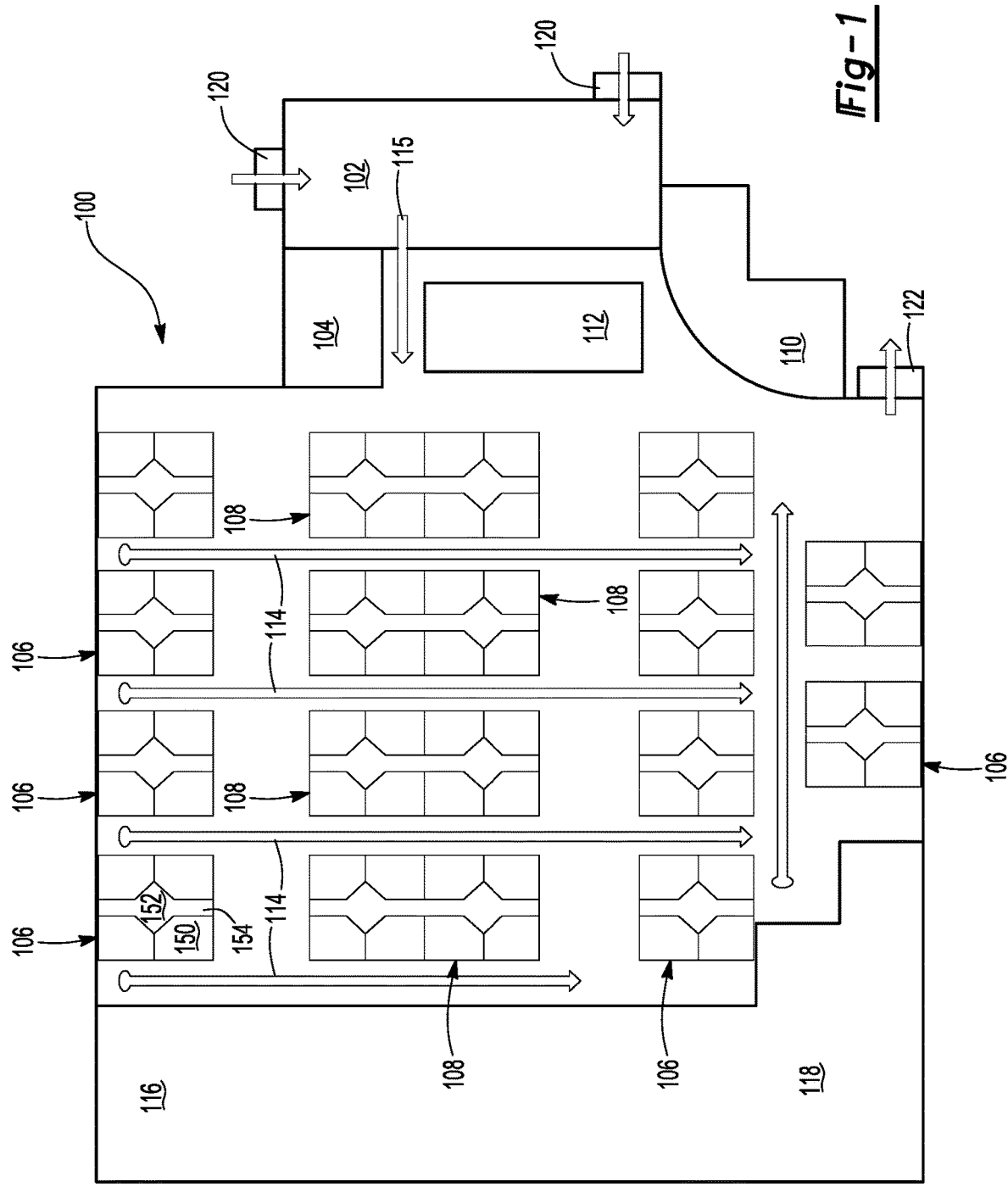

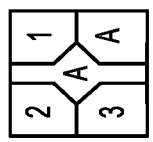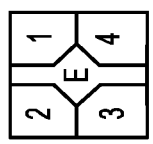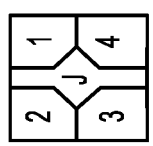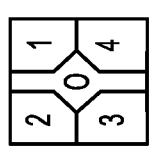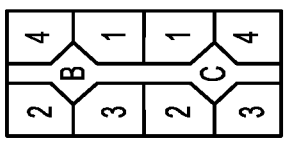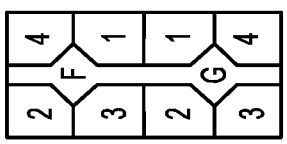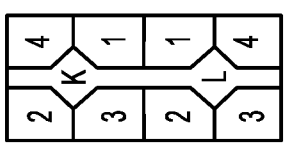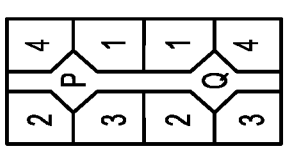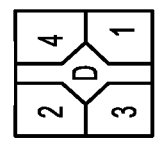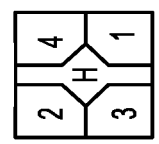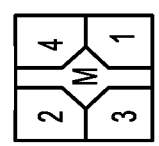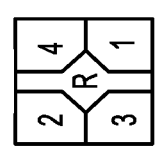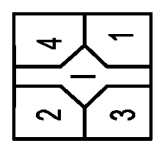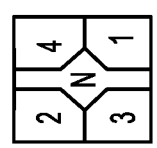
Fig-3

CLINIC DESIGN AND CORRESPONDING PATIENT ENGAGEMENT TOOL

CROSS REFERENCE TO RELATED APPLICATIONS

The application claims priority and benefit to U.S. provisional application Ser. No. 62/569,737 filed on Oct. 9, 2017.

TECHNICAL FIELD

The present specification generally relates design for a medical clinic. This innovative medical clinic is comprised of a unique room design and an integrated patient engagement tool. The patient engagement tool includes both a computer program and corresponding mobile device application. Together the room design and patient engagement tool both relate to enhancing patient involvement, improving medical care delivery, and fostering patient health education.

BACKGROUND

In the medical field, it is standard to have a primary care physician office fully separate and spaced apart from any specialist physician. As is standard, a patient will first visit a primary care physician and then, if required, be referred to a specialist. The patient must then make an appointment with that specific specialist, often many months later. If desired, the patient must then make a separate appointment with another specialist for a second opinion.

As a background in one application of medicine, vascular healthcare is examined. Cardiovascular disease is a leading cause of death in North America and has become a public health epidemic. Cardiovascular disease and the associated risk factors are linked to an increased risk of morbidity and mortality and are also responsible for escalating healthcare costs. Traditionally, if a primary care physician thinks that a patient should be examined by a cardiologist, the patient is referred to a cardiologist and must make an appointment with the cardiologist's office, often at an entirely different location. When a second opinion is desired, as is often the case, the patient is again responsible for making an appointment. This system delays healthcare delivery to the patient, is time consuming, inconvenient and very costly. Separate EMRs (electronic medical records), and poor information sharing adds to the dysfunctional delivery of care. The current system is highly disjointed and inefficient for practitioners and patients alike.

Typically, a high risk vascular patient must visit several different specialist physicians (cardiologist, endocrinologist, nephrologist, etc.), medical laboratories, imaging facilities, a pharmacy, and their primary care physician. Usually, each of these encounters occurs at different locations and together comprise basic healthcare. The clinical information from each of these separate encounters is not readily available to the individual healthcare providers and is almost always not available to the patient. This process results in the patient being less involved in their healthcare decisions. The patient is further burdened with the responsibility of coordinating multiple appointments (and time away from work) to manage their health.

Accordingly, improved approaches are needed within healthcare systems to address this epidemic and improve patient education, attendance, and adherence to strategies known to improve health outcomes while limiting financial burden. As such, a need exists in an improved medical clinic design, enhanced by multispecialty care and integrated technologies suited to optimizing the patient's time in clinic and healthcare involvement and overall health outcomes.

SUMMARY

The present specification discloses a medical clinic design with a unique layout, corresponding computer program and companion mobile device application. The broad specification for the present specification relates to a physical layout for a medical clinic design including a waiting room, reception area, modular clinic pods containing patient exam rooms, pharmacy, laboratory . . . etc. along with corresponding flow arrows illustrating the optimization of clinic flow, thereby increasing clinic efficiency. The present application includes a physical and operational design for a medical clinic, by way of example, and an integrated patient engagement tool (computer program and companion mobile device application). These components are specifically fashioned to work synergistically to improve the efficiency of healthcare delivery, and outcomes in patients with vascular disease or the associated risk factors.

In one embodiment, a medical clinic is provided including a plurality of modular pods wherein each pod includes a plurality of patient exam rooms and a dedicated workspace wherein at least one of the plurality of modular pods is configured for a general practice physician and at least one of the plurality of modular pods is configured to a specialist physician.

In another embodiment, a modular pod designed for use in a medical clinic is provided, the modular pod being fully contained with a plurality of walls, the modular pod having a plurality of patient exam rooms, a dedicated workspace surrounded by the plurality of patient exam rooms wherein the plurality of patient exam rooms are accessible via said workspace and externally so as to facilitate patient and physician movement within the medical clinic.

In yet another embodiment, a system is provided that is configured to enhance patient engagement through the unique dissemination of information from clinic personnel to patients. A patient engagement tool comprised of a computer program and mobile device application where the computer program is separate from, but works in conjunction with, the mobile device application. This system is configured to translate information inputted into the computer program, by clinic personnel, such as but not limited to, problem list, educational material, medication list, and appointment information, to QR code format. The companion mobile device application will contain a QR code detection function configured to capture a QR code by means of the camera of a mobile device. The individualized, uniquely generated, information containing QR code will be translated by the mobile device application. The mobile device application having the ability to interpret each unique QR code will allow the mobile device application to display the appropriate problem list, educational material, medication list and/or appointment information specifically geared to the user of the mobile device application.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 1 depicts an exemplary medical clinic layout having a waiting room, lab, reception, primary care pods, specialist pods and a pharmacy with illustrative flow arrows extending therethrough according to one or more embodiments shown and described herein;

FIG. 3 depicts an exemplary flow manager screen accessible within the computer program to clinic personnel configured to allow indication and communication of patient exam room occupancy and allows the implementation of the 'quick' consult model according to one or more embodiments shown and described herein;

DETAILED DESCRIPTION

Figure 2A:
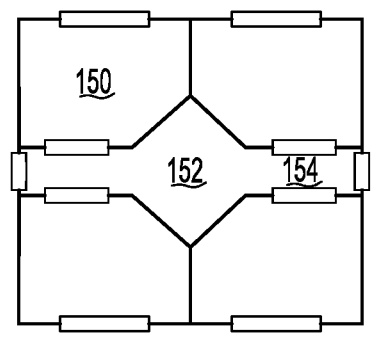
FIG. 2a depicts an exemplary exploded view of a single modular pod (comprised of 4 patient exam rooms and a dedicated work space) according to one or more embodiments shown and described herein.

The present specification discloses a medical clinic layout, corresponding computer program and companion mobile device application. FIG. 1 generally depicts a physical layout for a medical clinic design including a waiting room, reception area, modular clinic pods, patient exam rooms, physician workspace, pharmacy, laboratory . . . etc. along with corresponding flow arrows to illustrate the optimization of the clinic's efficiency. The present application includes a unique physical and operational design for a vascular health clinic, by way of example, and an integrated computer program with a companion mobile device application. These components are specifically fashioned to work synergistically to increase the efficiency of health care delivery and improve health outcomes in patients with vascular disease and the associated risk factors.

The design of the present application is configured to eliminate the fundamental problems, as previously described, with the current healthcare model. Patients will have access to their primary care physician, a select group of vascular health specialists, including cardiology, nephrology, endocrinology, neurology, and vascular surgery (available on-demand for 'quick' problem specific consultation), a medical laboratory, imaging, diagnostics, and pharmacy services, all at the same location, and in the same visit. A corresponding computer application and companion mobile device application are also provided.

By implementing the below described design and utilizing the corresponding computer program and companion mobile device application, healthcare providers will be able to increase the efficiency and quality of healthcare delivery, facilitate and simplify coordination of care, enhance patient involvement in healthcare and measure and improve health outcomes in patients with vascular disease through clinical evidence-based strategies. By implementing this complete design, a new gold standard of healthcare will be achieved.

Referring now to FIG. 1, a medical clinic 100 is provided having a waiting room 102, reception 112, a lab 104, a plurality of primary care modular pods 106 (a pod is comprised of 4 exam rooms, a central workspace and access hallways), specialist modular pods 108 (a pod is comprised of 4 exam rooms, a central workspace and access hallways), a pharmacy 110, entrance 120 and exit 122.

Referring now to FIG. 1, the clinic's lab will be available for immediate blood drawing prior to the patient's appointment. Analysis of the blood sample will take approximately 10-15 minutes and results will be electronically inputted into the clinic's EMR (electronic medical record). The results will be available to the healthcare provider that same day for assessment. This saves the patient a visit to separate medical laboratory, which is common practice, usually done one week prior to their clinic appointment.

Figure 2B:
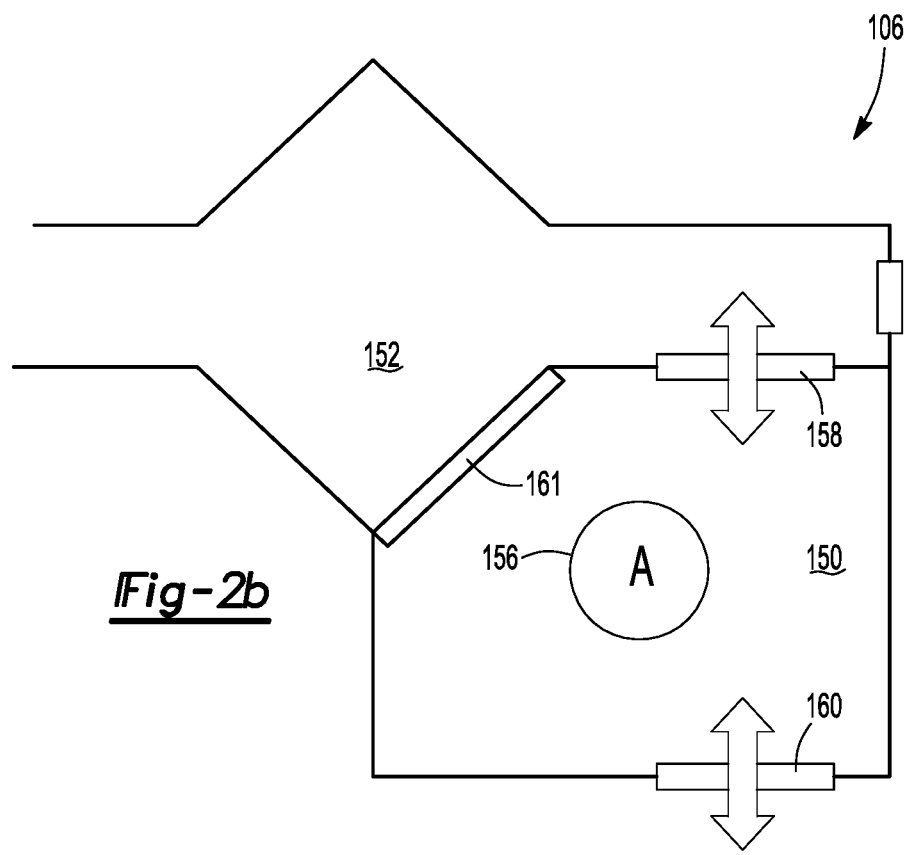
FIG. 2b depicts an exemplary exploded patient exam room and dedicated work space with access corridors designed according to one or more embodiments shown and described herein.

Each of primary care modular pods 106 and the specialist modular pods 108 include a centralized work area 152 surrounded by four exam rooms 150, giving the provider easy access to each exam room through the access hallways. Each of the exam rooms 150 has a separate entrance/exit for the provider 158 (FIG. 2b) and a separate entrance/exit for the patient 160 (FIG. 2b). The provider also has a separate entrance/exit to the work area 154 (FIG. 1 and FIG. 2). The plurality of entrances and exits (as shown by the plurality of doors in FIGS. 2a and 2b) for the patients and physicians optimizes efficiency of the modular pods, and therefore the entire medical clinic. Each of the exam rooms in the clinic are compartmentalized, patient-centered, and facilitate a collaboration between healthcare providers and patients. Each exam room will have a unique and uniform design.

The pods 106 are positioned adjacent to one another. Each of the pods 106 has a hallway extending therethrough to optimize movement of healthcare providers between exam rooms, and to enable specialist physicians from the pods 108 to easily access the pods 106 for 'quick' consultation.

The joint specialist pods 108 contain at least two work spaces for physicians. The dual workspace configuration allows two specialists to work directly adjacent to one another, allowing optimization of patient care. If, for example, the patient or physician wants a second opinion, a similarly specialized physician is available to immediately provide a second opinion. This method of providing second opinions can be applied to the primary care physicians as well. All physicians, both primary care and specialist, can utilize the centralized hallways connecting the work spaces and enter through the physician entrances, to increase efficiency of movement throughout the clinic.

Each exam room will have a dedicated area for the use of audio/visual presentation 161 (FIG. 2b), which allows the patient to see their laboratory values, imaging results, and question their healthcare provider with any concerns. This design allows the patient to be more involved in their healthcare decisions, and more informed about their condition. The audio/visual presentation 161 (FIG. 2b) will display educational material while the patient waits for the physician in the exam room. The use of audio/visual technology 161 (FIG. 2b) is also integrated with the use of the novel computer program and companion mobile device application. When a healthcare provider generates a QR code 254 (FIG. 5) using the computer program, it will be displayed on the projection area for the patient to scan using the companion mobile device application.

The patient will scan the QR code 254 (FIG. 5), giving them access to their problem list and educational materials, such as outlined and described in the forgoing description of the computer program and companion mobile device application. The QR code 254 may also open a link to download/view additional information critical to the patient and patient care. The exam room will contain a single swivel, examination chair in the center of the room, as well as a rolling chair for the attending physician. Other components standard and necessary in typical exam rooms may also be provided.

The medical clinic may also be equipped with a paging system, to facilitate the 'quick' consult model. In each exam room audio/visual educational material will be displayed on the screen 161 until the physician arrives. In this embodiment, the screen 161 is contained within the exam room. The screen may be any display screen, such as a monitor, projector or television, suitable to provide the relevant information to the patient.

In one aspect of the present specification, a means for enabling communication within the medical clinic regarding the occupancy of exam rooms is provided. The computer program will have a secure login for all clinic personnel (both support staff and healthcare providers). This function of the computer program can be described as a flow manager and will also facilitate the novel 'quick' consult model. This function will be available from the computer program home screen and when accessed will lead to the screen as disclosed herein in FIG. 3. This screen will be accessible to all clinic members (both support staff and healthcare providers). By clicking the pictorial representation of an exam room, a clinic member will have the option to change the occupancy status of that exam room. The status options are: empty, filled-ready for nurse, filled-ready for doctor, filled-patient and doctor, as illustrated in FIG. 3. The exam room statuses are color coordinated, as shown in FIG. 3, to make the status of the exam room visually detectable by clinic personnel. When an exam room's status is changed, the computer program will notify appropriate clinic personnel in two ways. The first notification method is a pop-up desktop notification, and the second is a mobile device notification. Combined, the flow manager, and notification systems will maximize clinic efficiency.

The next novel component of the flow manager is making the 'quick' consult model practical and functional. A healthcare provider will be able to select an exam room where they would like a colleague's consultation. Once the room is selected, a specific provider can be chosen for consultation. The provider chosen for consultation will then receive notification via the computer program in the form of a desktop notification and a mobile device notification.

The computer program and companion mobile device application, such as illustrated in FIGS. 4-7, are essential to accomplishing the goals of the medical clinic by increasing productivity and improving patient health outcomes. The computer program and companion mobile device application work together to enhance coordination of care, increase patient involvement in care, while also providing helpful educational material, and simultaneously integrating clinic design with novel technology such as described herein and above. The problem list, medication list, educational material, appointment information and reminders will also be instrumental in increasing patient involvement, medication adherence and patient appointment compliance. These features are available to the patient through the companion mobile device application on the patient's personal mobile device. A detailed explanation of each component is found below.

Figure 4:
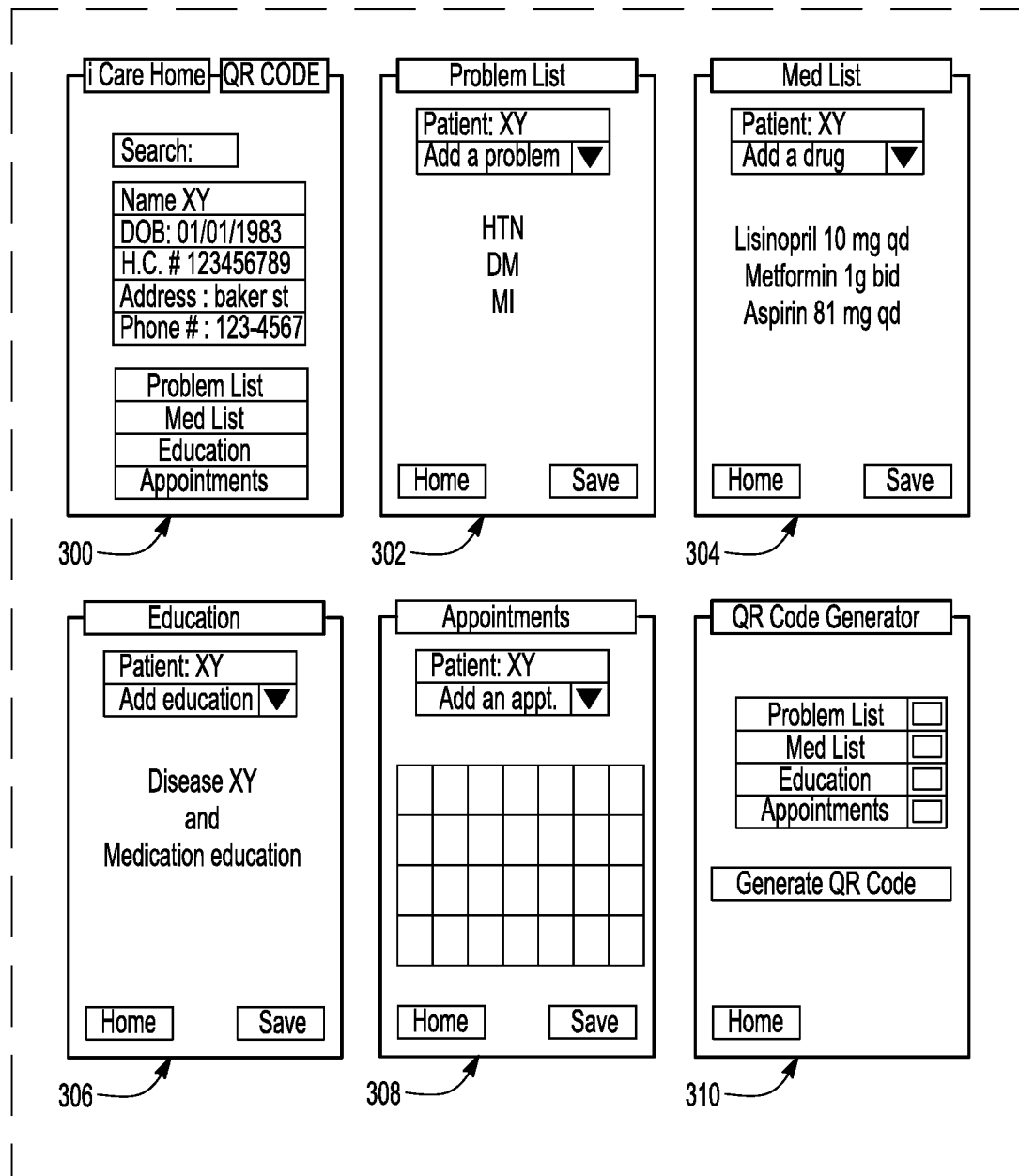
FIG. 4 depicts exemplary screen shots of the computer program model showing information inputted by clinic personnel including patient identification information, problem list, medication list, educational material, appointments and the QR code generator according to one or more embodiments shown and described herein.

FIG. 4 illustrates the general interface of the computer program for healthcare providers and medical clinic personnel. FIG. 4 generally illustrates exemplary screen shots of the computer program. The first screen 300 includes general biographical information such as the date of birth, address . . . etc. of the patient and accessible functions such as problem list, medication list, education, and appointments. This information is inputted by the physician or the medical clinic personnel. Screens 302, 304, 306 and 308 all illustrate areas for the healthcare team to input information such as the problem list, medication list, education and appointments, respectively. Screen 310 illustrates the QR code 254 generator.

FIG. 4 shows a general layout of the computer program, in which each clinic patient will have a profile with basic identification information (name, DOB, gender, address, phone number, health coverage identifiers . . . etc.). Within each profile, one of four functions can be accessed 300. The functions include the problem list 302, medication list 304, education 306, and appointments 308. As described below, within each of these four categories, information can be selected/inputted by the health care team that is specifically suited to each patient. Once the information is inputted by the appropriate personnel, the information is saved to the patient's profile allowing a QR code to be generated and scanned by the patient via the companion mobile device application on the patient's personal mobile device. Once scanned the patient will have access to information and reminders that will increase patient involvement and improve health outcomes.

Figure 5:
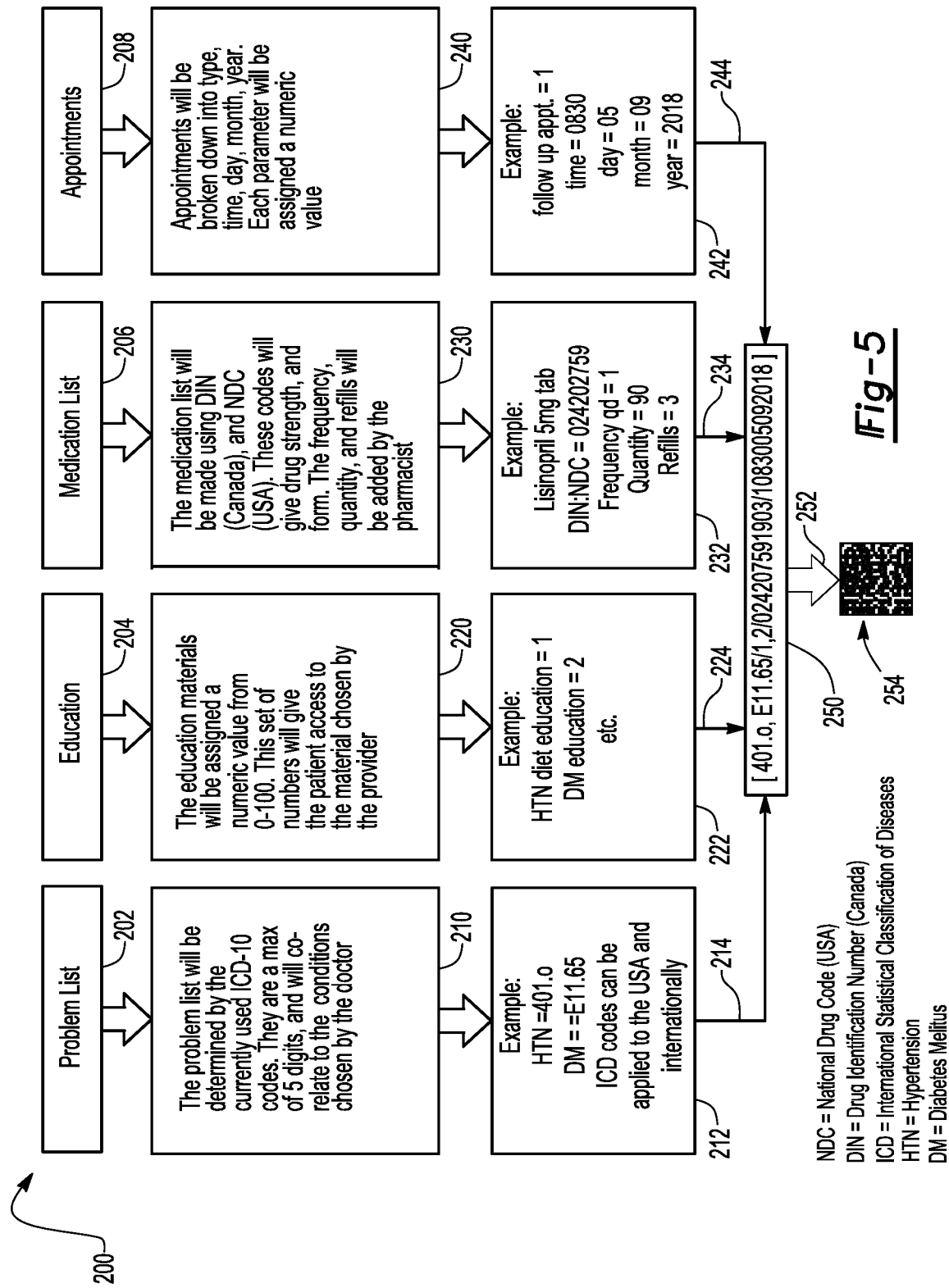
FIG. 5 depicts an exemplary flow chart of the computer program process of QR code synthesis according to one or more embodiments shown and described herein.

FIG. 5 illustrates a general process in accordance with the computer program QR code synthesis 200. The problem list 202 is inputted by the provider to grant the patient a current, inclusive problem list available to the patient on their personal mobile device via the companion mobile device application. The provider inputted problem list will computationally be translated to the appropriate, currently used ICD-10 (International Classification of Diseases) codes. This process is illustrated beginning at reference numeral 202. An example of ICD-10 codes are provided in the flow chart of FIG. 5 at reference numeral 212. The selected problems are inputted and converted to ICD-10 codes, then they are combined 214 (as illustrated by the directional arrow) into the numerical code 250. This numerical code 250 is generated 252 into a QR code 254, such as shown.

FIG. 5 further illustrates the education 204 selected by the physician granting the patient access to the corresponding educational material on their personal mobile device via the companion mobile device application. The educational material is selected by the physician specifically suited to each patient. All distinct educational material will have an assigned numeric value as shown in reference numeral 220. Reference numeral 222 illustrates an example of these assigned numeric values. The provider selected educational material are computationally translated to their numeric value and combined 224 (as illustrated by the directional arrow) into the numerical code 250. This numerical code 250 is generated 252 into a QR code 254, such as shown.

FIG. 5 further illustrates a medication list 206 is further provided as inputted by the pharmacist, granting the patient access to their medication list and compliance reminders on their personal mobile device via the companion mobile device application. As illustrated by reference numeral 230 in FIG. 5, the medication list is formulated using DIN (Drug Identification Number—Canada) and NDC (National Drug Code—USA). These codes give the drug, strength and form. The quantity, dosing frequency, route of administration and refills may also be added to this information. An exemplary set of codes is provided at reference numeral 232 showing an exemplary drug, strength, form, quantity, frequency, and refills . . . etc. The pharmacist will input the medication list which will be computationally converted into a unique numeric code and combined 234 (as illustrated by the directional arrow) into the numerical code 250. This numerical code 250 is generated 252 into a QR code 254, such as shown.

FIG. 5 further illustrates the appointments 208 are inputted by the physician or support staff and viewable by the patient on their mobile device via the mobile application. As illustrated at reference numeral 240, appointments are broken down into type, time, day, month and year. To generate the QR code 254, each parameter of the appointment is computationally assigned a numeric value. An exemplary set of numeric values is illustrated at reference numeral 242. The appointments are inputted and computationally converted into a unique code and combined 244 (as illustrated by the directional arrow) into the numerical code 250 This numerical code 250 is generated 252 into a QR code 254, such as shown.

Collection of data as outlined above and as outlined in FIG. 4 and FIG. 5 allows the computer program to generate the QR code 254 that is readable by the companion mobile device application. The QR codes 254 are made available to the patient in the exam room, at reception, or in the pharmacy, electronically or in any way deemed effective and efficient.

Figure 6:
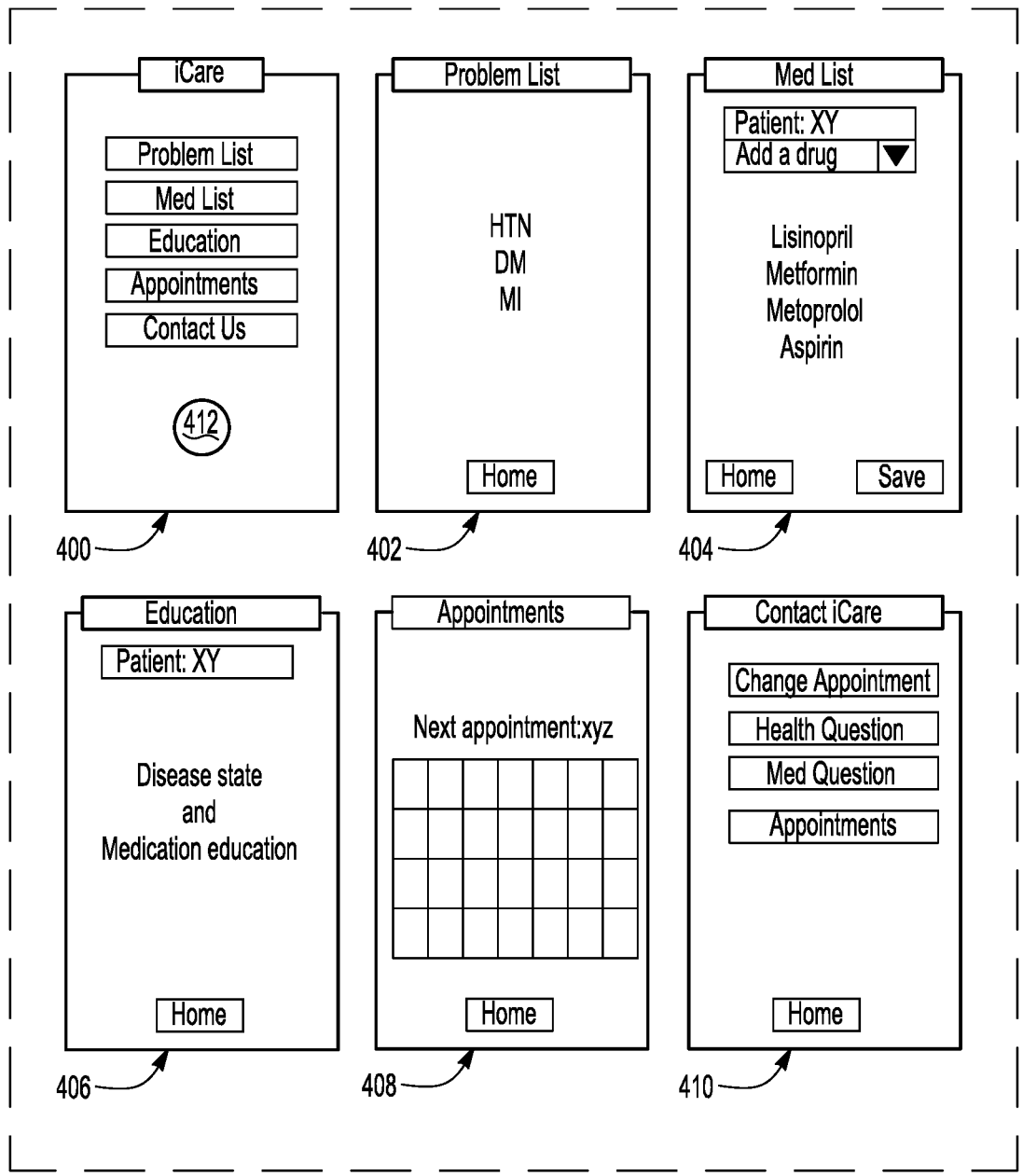
FIG. 6 depicts exemplary screen shots of the companion mobile device application model including information accessible to the patient such as, but not limited to, problem list, medication list, educational material, and appointment information according to one or more embodiments shown and described herein.

FIG. 6 illustrates the general user interface of the companion mobile device application. Screen 400 having the button 412 (to enable the camera to capture the QR code). Screen 400 also enumerates the selectable options of problem list, medication list, education, appointments or contact us. Screen 402 illustrates the problems list, screen 404 illustrates the medication list 404, screen 406 illustrates the educational material available to the patient, screen 408 depicts upcoming appointments and screen 410 shows contact options.

Figure 7:
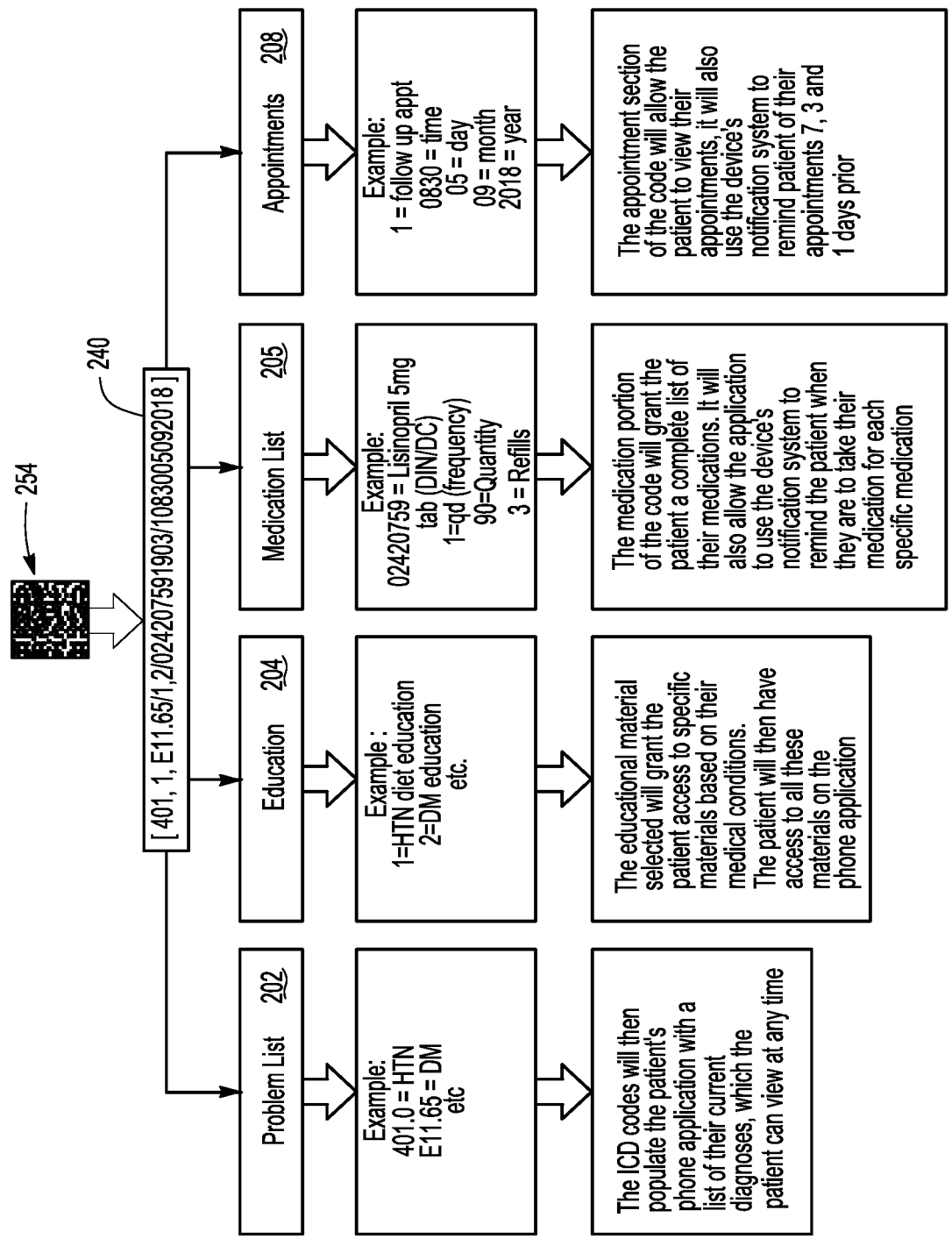
FIG. 7 depicts an exemplary flow chart of the process of decoding of a synthesized QR code by the companion mobile device to one or more embodiments shown and described herein.

The companion mobile device application utilizes the camera function 412 in virtually all mobile devices to read the QR code 254. Upon downloading the companion mobile device application, the patient will be able to scan the QR code 254 provided to them by clinic personnel. The companion mobile device application will open with the camera function enabled. The user can tap the circle 412 while the camera is in view of the QR code 254 to allow for QR code decoding (FIG. 7). The companion mobile device application will automatically populate with the information (problem list, medication list, educational material, and appointments) attached to that unique QR code. The information previously translated into the QR code 254 will be accessible to the patient within the companion mobile device application. The companion mobile device application will subsequently provide helpful reminders for medication adherence, medication refills, and appointments. The companion mobile device application will access the devices' notification system and remind patients of upcoming appointments 7 days, 3 days, and 1 day prior to their appointment. This allows for more efficient use of office staff time by eliminating the need to make appointment reminder calls, while enhancing appointment attendance. The application will also provide medication adherence reminders. The reminders will be specific to the drugs and medication schedule that the patient is prescribed. This will improve adherence to therapies known to improve patient health outcomes. Furthermore, the companion mobile device application will have a function allowing the patient to contact the clinic via email 410. This function will be stratified, allowing the patient to select the general purpose of their inquiry. Each selection will open a template email and allow the patient to send their comment/question/concern to a generalized email account(s) and include their phone number for correspondence. Emails will be sorted by importance and urgency, and promptly responded to accordingly. The companion mobile device application will eventually be developed to allow the patient to track their home health information, such as blood pressure, blood sugar readings, etc. and pertinent clinical laboratory parameters.

It is noted that the terms "substantially" and "about" may be utilized herein to represent the inherent degree of uncertainty that may be attributed to any quantitative comparison, value, measurement, or other representation.

These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter.

Moreover, although various aspects of the claimed subject matter have been described herein, such aspects need not be utilized in combination.

It is therefore intended that the appended claims cover all such changes and modifications that are within the scope of the claimed subject matter.

What is claimed is:

1. A medical clinic configuration comprising:
    a plurality of modular pods wherein each pod includes a plurality of patient exam rooms and a dedicated workspace with access hallways wherein at least one of the plurality of modular pods is configured for a general practice physician and at least one of the plurality of modular pods is configured to a specialist physician, the primary care physicians, specialists, pharmacist, and all clinic personnel work together within the same physical clinic space and operational model to provide a higher quality of healthcare to patients, each of the modular pods including the plurality of patient exam rooms and the dedicated works space all being self-contained.

2. The medical clinic of claim 1 wherein a reception area, medical laboratory, and pharmacy are positioned on a sequential path configured to enhance the efficiency of patient movement from the reception area to the plurality of modular pods and to other healthcare related services.

3. The medical clinic of claim 1 wherein each modular pod includes a hallway extending therethrough with a central dedicated workspace.

4. A modular pod designed for use in a medical clinic, the modular pod being fully contained with a plurality of walls, the modular pod comprising:

a plurality of patient exam rooms;

a centralized physician workspace and hallway at least partially surrounded by the plurality of patient exam rooms;

the plurality of patient exam rooms accessible via said physician workspace and hallway internally and externally so as to facilitate patient and physician movement between the patient exam rooms and the physician office.

5. The modular pod of claim 4 wherein each patient exam room within the modular pod having a display screen configured to enhance the provider-patient interaction where the display screen is used facilitate use of a corresponding computer program and companion mobile device application.

6. A self-contained modular pod for use in a medical clinic, the modular pod comprising:

four exterior walls forming the exterior footprint of the self-contained modular pod, the four exterior walls forming 4 internal corners;

a hallway extending between two walls of the four exterior walls, the hallway extending between two of the exterior walls that are parallel to each other, the hallway having a first care provider entrance/exit and a second care provider entrance/exit, each of the first care provider entrance/exit and the second care provider entrance/exit positioned on the exterior walls;

four exam rooms positioned in each of the 4 corners, each of the exam rooms having a dedicated care provider entrance/exit to said hallway, each of the exam rooms having a dedicated patient entrance/exit in one of the exterior walls, said hallway separating a first set of two exam rooms from a second set of two exam rooms; and a centralized physician workspace, the centralized physician workspace surrounded by and sharing an angled wall with each of the four exam rooms so as to expand the area of the centralized physician workspace.

7. The self-contained modular pod for use in a medical clinic of claim 6 wherein two self-contained modular pods are combined together wherein the hallways of each modular pod are connected to form a singular large hallway.

\* \* \* \* \*